(12) United States Patent
Wagner et al.

(10) Patent No.: US 7,790,769 B2
(45) Date of Patent: Sep. 7, 2010

(54) MEROCYANINE DERIVATIVES

(75) Inventors: Barbara Wagner, Lörrach (DE); Astrid Walther, Grenzach-Wyhlen (DE); Bernd Herzog, Grenzach-Wyhlen (DE)

(73) Assignee: Ciba Corporation, Tarrytown, NY (US)

( * ) Notice: Subject to any disclaimer, the term of this patent is extended or adjusted under 35 U.S.C. 154(b) by 113 days.

(21) Appl. No.: 12/086,647

(22) PCT Filed: Dec. 11, 2006

(86) PCT No.: PCT/EP2006/069516

§ 371 (c)(1),
(2), (4) Date: Jun. 17, 2008

(87) PCT Pub. No.: WO2007/071582

PCT Pub. Date: Jun. 28, 2007

(65) Prior Publication Data

US 2009/0169495 A1   Jul. 2, 2009

(30) Foreign Application Priority Data

Dec. 20, 2005   (EP) .................... 05112477

(51) Int. Cl.
*A61K 31/136*   (2006.01)
*C07C 211/26*   (2006.01)

(52) U.S. Cl. .................... 514/579; 564/462

(58) Field of Classification Search .................... None
See application file for complete search history.

(56) References Cited

U.S. PATENT DOCUMENTS

2005/0255055 A1   11/2005   Wagner et al. .................. 424/59

FOREIGN PATENT DOCUMENTS

| GB | 2409203 | 6/2005 |
| GB | 2416351 | 1/2006 |
| WO | 2004/006878 | 1/2004 |
| WO | 2005/058269 | 6/2005 |
| WO | 2007/014848 | 2/2007 |

OTHER PUBLICATIONS

K. Dahlqvist et al., Acta Chem. Scand. 24, No. 6, (1970), pp. 2075-2083.

*Primary Examiner*—Kamal A Saeed
*Assistant Examiner*—Michael Barker
(74) *Attorney, Agent, or Firm*—Mervin G. Wood

(57) ABSTRACT

Disclosed are merocyanine derivatives of formula (1), wherein $R_1$ and $R_2$ independently from each other are branched $C_4$-$C_{22}$alkyl; or branched $C_4$-$C_{12}$ alkenyl; $R_3$ and $R_4$ independently from each other are cyano; $COR_7$, $COOR_7$; $CONR_7R_8$; $SO_2(C_6$-$C_{12})$aryl; $C_2$-$C_{12}$alk-1-enyl; $C_3$-$C_{12}$cycloalk-1-enyl; $C_2$-$C_{12}$alk-1-inyl; $C_2$-$C_{12}$heteroalkyl; $C_3$-$C_5$heterocycloalkyl; $C_6$-$C_{10}$aryl; or $C_1$-$C_9$heteroaryl; wherein at least one of $R_3$ and $R_4$ is cyano; $R_5$ and $R_6$ independently from each other are hydrogen; $C_1$-$C_6$alkyl; $C_5$-$C_8$cycloalkyl which may be substituted by one or more than one $C_1$-$C_4$alkyl; and $R_7$ and $R_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; —$(CH_2)_x$COOH; $C_7$-$C_{12}$aralkyl; $C_1$-$C_{12}$heteroalkyl; $C_2$-$C_{11}$heteroaralkyl; $C_6$-$C_{10}$aryl; $C_1$-$C_9$heteroaryl. The compounds are useful as UV absorbers for protecting human hair and skin against the damaging effect of UV radiation.

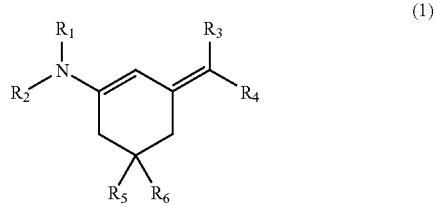

(1)

5 Claims, No Drawings

MEROCYANINE DERIVATIVES

The present invention relates to the compounds of formula

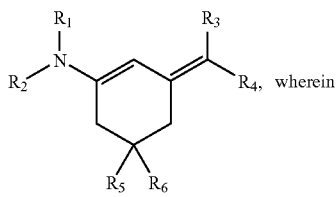

(1)

wherein $R_1$ and $R_2$ independently from each other are branched $C_4$-$C_{22}$alkyl; or branched $C_4$-$C_{12}$alkenyl;

$R_3$ and $R_4$ independently from each other are cyano; $COR_7$, $COOR_7$; $CONR_7R_8$; $SO_2(C_6$-$C_{12})$aryl; $C_2$-$C_{12}$alk-1-enyl; $C_3$-$C_{12}$cycloalk-1-enyl; $C_2$-$C_{12}$alk-1-inyl; $C_2$-$C_{12}$heteroalkyl; $C_3$-$C_5$heterocycloalkyl; $C_6$-$C_{10}$aryl; or $C_1$-$C_9$heteroaryl; wherein at least one of $R_3$ and $R_4$ is cyano;

$R_5$ and $R_6$ independently from each other are hydrogen; or $C_1$-$C_6$alkyl; and $R_7$ and $R_8$ independently from each other are hydrogen; $C_1$-$C_{22}$alkyl; $C_2$-$C_{12}$alkenyl; $C_2$-$C_{12}$alkinyl; $C_3$-$C_{12}$cycloalkyl; $C_3$-$C_{12}$cycloalkenyl; —$(CH_2)_t$COOH; $C_7$-$C_{12}$aralkyl; $C_1$-$C_{12}$heteroalkyl; $C_2$-$C_{11}$heteroaralkyl; $C_6$-$C_{10}$aryl; $C_1$-$C_9$heteroaryl.

Alkyl (for the definitions of $R_5$, $R_6$, $R_7$ and $R_8$), cycloalkyl, alkenyl or cycloalkenyl may be straight chained or branched, monocyclic or polycyclic.

Alkyl is for example methyl, ethyl, n-propyl, isopropyl, n-butyl, sec.-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Examples for branched alkyl (for the definitions of $R_1$ and $R_2$) are 1-methylpropyl; 1,3-dimethylbutyl; 2-methylbutyl; 1,1,3,3-tetramethylbutyl; 3-methylbutyl; 7-methyloctyl; 2-ethylhexyl; or 4-methylcyclohexyl.

Alkenyl is for example straight-chain $C_2$-$C_{12}$alkenyl or preferably branched $C_3$-$C_{12}$alkenyl like vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the different isomers of hexenyl, octenyl, nonenyl, decenyl oder dodecenyl.

$C_5$-$C_8$cycloalkyl is for example, cyclopentyl, trimethylcyclohexyl, cyclooctyl or preferably cyclohexyl.

$C_1$-$C_9$heteroaryl is an unsaturated or aromatic radical having $4n+2$ conjugated $T$-electrons, for example 2-thienyl, 2-furyl, 2-pyridyl, 2-thiazolyl, 2-oxazolyl, 2-imidazolyl, isothiazolyl, triazolyl, tetrazolyl or another ring system selected from thiophene-, furan-, pyridine, thiazol, oxazol, imidazol, isothiazol, triazol, pyridine- and benzene rings, which are unsubstituted or substituted by 1 to 6 ethyl, methyl, ethylene and/or methylene, like benzotriazolyl, in the case of N-heterocycles optionally in the form of their N-oxides.

Preferred are compounds of formula (1), wherein
$R_1$ and $R_2$ independently from each other are branched $C_4$-$C_{22}$alkyl; or branched $C_4$-$C_{12}$ alkenyl;

$R_3$ and $R_4$ independently from each other are cyano; $COR_7$, $COOR_7$; $CONR_7R_8$; $SO_2(C_6$-$C_{12})$aryl;

$R_5$ and $R_6$ independently from each other are hydrogen; $C_1$-$C_6$alkyl; $C_5$-$C_8$cycloalkyl which may be substituted by one or more than one $C_1$-$C_4$alkyl; and $R_7$ and $R_8$ independently from each other are hydrogen; or $C_1$-$C_{22}$alkyl.

More preferred compounds of formula (1) are those, wherein $R_3$ is cyano;

$R_4$ is cyano; $COR_7$, $COOR_7$; $CONR_7R_8$; $SO_2(C_6$-$C_{12})$aryl; and $R_1$, $R_2$, $R_5$, $R_6$, $R_7$ and $R_8$ are defined as in formula (1).

Most preferred are compounds of formula (1), wherein $R_1$ and $R_2$ are identical; and $R_3$, $R_4$, $R_5$ and $R_6$ are defined as in formula (1).

Preferably in formula (1)

$R_1$ and $R_2$ are selected from 1-methylpropyl; 1,3-dimethylbutyl; 2-methylbutyl; 1,1,3,3-tetra-methylbutyl; 3-methylbutyl; 7-methyloctyl; 2-ethylhexyl; 4-methylcyclohexyl; and 2-methyl-2-propene.

More preferred are compounds of formula (1), wherein $R_3$ and $R_4$ are —C≡N.

Also preferred are compounds of formula (1), wherein $R_3$ is —C≡N;

$R_4$ is $COR_7$, $COOR_7$; $CONR_7R_8$; or $SO_2(C_6$-$C_{12})$aryl; and $R_7$ and $R_8$ are $C_1$-$C_4$alkyl.

Examples of cyclic merocyanine derivatives according to the present invention are listed in Table 1:

TABLE 1

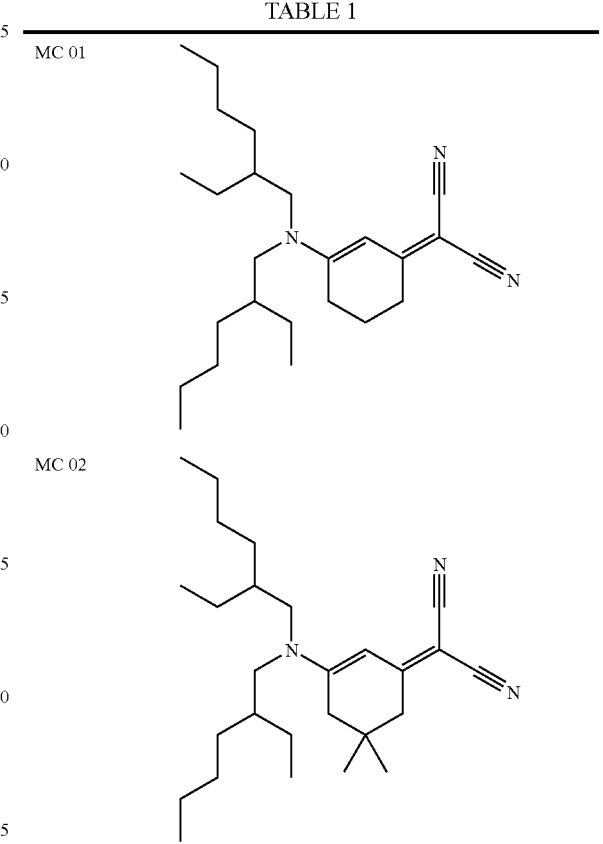

MC 01

MC 02

TABLE 1-continued
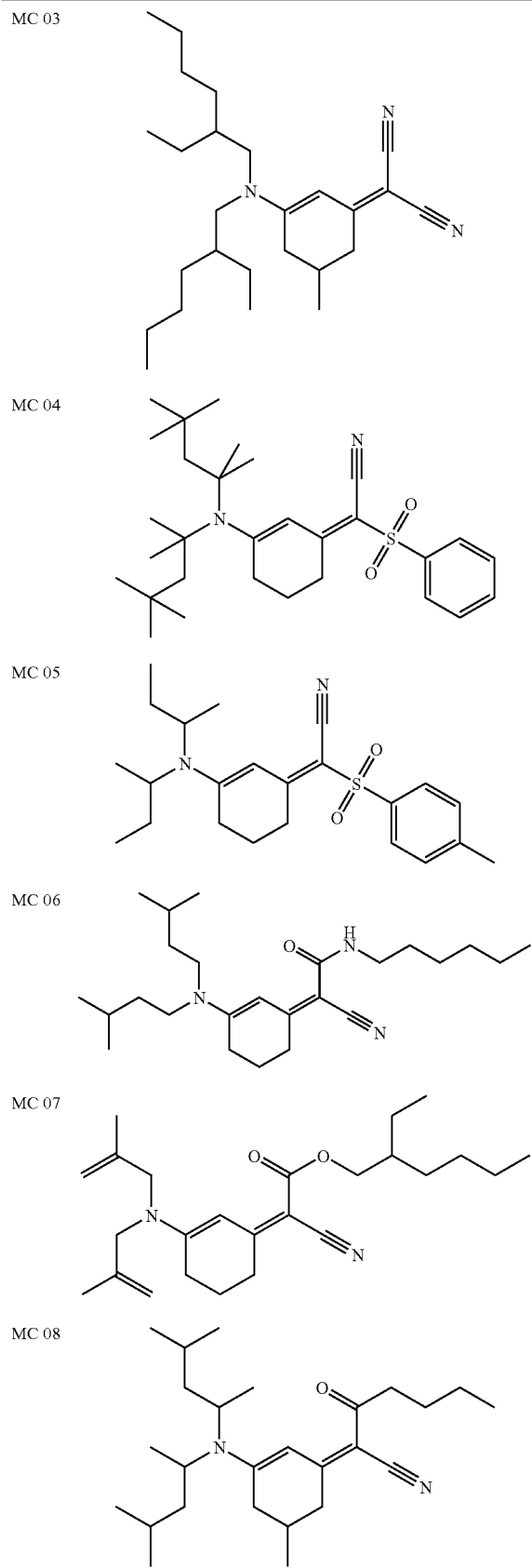
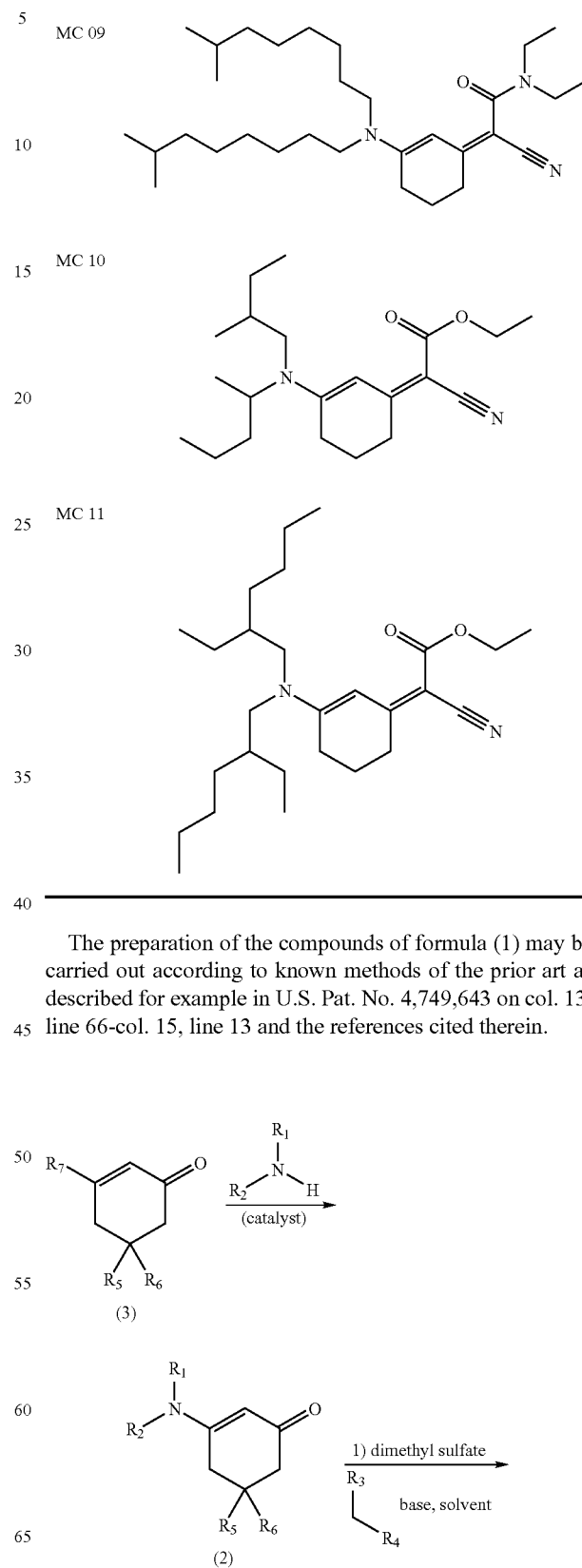
The preparation of the compounds of formula (1) may be carried out according to known methods of the prior art as described for example in U.S. Pat. No. 4,749,643 on col. 13, line 66-col. 15, line 13 and the references cited therein.

-continued

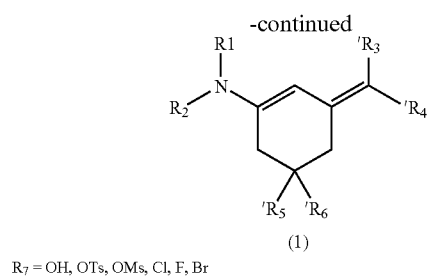

R$_7$ = OH, OTs, OMs, Cl, F, Br

The compounds of formula (1) can be prepared starting from 1-aminocyclohexanone-3 of the formula

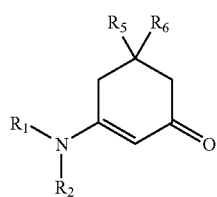

which is alkylated with dimethylsulfate or with another alkylating agent like diethylsulfate or methyliodide.

In a second step the reaction mixture is treated with the methylene active compound $CH_2R_3R_4$ in the presence of a base. The compound of formula (2), the alkylating agent, $CH_2R_3R_4$ and the base are reacted in approximately equimolar proportions.

Sometimes an excess of the alkylating agent, $CH_2R_3R_4$ and the base related to the compound of formula (2) are preferred.

The alkylation reaction of the starting compound of formula (2) with a suitable alkylating agent like dimethylsulfate may be carried out without using any solvent on in a suitable solvent, preferably in aliphatic or aromatic solvents like hexane, toluene, benzene or xylene. Protic solvents like methanol, ethanol, iso-butanol, tert-butanol or iso-propanol are also suitable. The reaction may also be carried out in dimethylsulfoxide, N-methylpyrrolidone, dimethylformamide or dimethylacetamide. Ether compounds like diethylether and tetrahydrofurane or halogenated solvents like chloroform or dichloromethane are also suitable solvents as well as mixtures of these solvents.

In the preparation method of the present invention the compound $CH_2R_3R_4$ is reacted in the presence of an inorganic or organic base. Typical examples of an organic base are amines like triethylamine, Hünig base, DBU (1,8-diazabicyclo[5.4.0]undec-7-ene), DBN (1,5-diazabicyclo[4.3.0]non-5-ene), p-dimethylaminopyridine and N,N,N',N'-tetramethylguanidine. Suitable bases are also alkoxides (e.g. sodium methoxide, sodium ethoxide, potassium t-butoxide).

Inorganic bases like NaH, LiOH and potassium carbonate are also suitable.

The reaction may be carried out at temperatures between −78° C. and the boiling point of the reaction mixture, preferably from 60 to 120° C.

The compounds of formula (2) can be prepared starting from 1-aminocyclohexanone-3 of the general formula

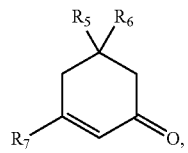

wherein R$_7$ is hydroxyl, ethoxy, methoxy, chlorine, bromine, fluorine, OTs (Ts is tosyl, —SO$_2$—C$_6$H$_4$—CH$_3$) or OMs (Ms is mesyl, —SO$_2$Me), which are condensed with a secondary amine R$_1$R$_2$NH.

The condensation reactions of the compounds of formula (2) with the compounds of formula (3) may be carried out according to known methods of the prior art as described for example in J. Org. Chem. 1981 (46) on pages 197-201, Synthesis, 1981, on pages 880-881, Acta Chemica Scandinavica, 1970 (24) on pages 2075-2083 or as described in the patent DE-614195 and the references cited therein.

The compounds of formula (2) are preferably prepared by the reaction of a cyclohexane-1,3-dion of formula (4)

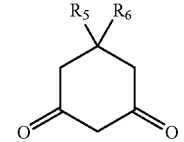

with a secondary amine R$_1$R$_2$NH in approximately equimolar proportions. The reaction is preferably carried out in an autoclave. The reaction may be carried out in a suitable solvent, preferably in aliphatic or aromatic solvents like hexane, toluene, benzene or xylene.

Protic solvents like methanol, ethanol, iso-butanol, tert-butanol or iso-propanol are also suitable. The reaction may also be carried out in dimethylsulfoxide, N-methylpyrrolidone, dimethylformamide or dimethylacetamide. Ether compounds like diethylether and tetrahydrofurane or halogenated solvents like chloroform or dichloromethane are also suitable solvents as well as mixtures of these solvents.

The reaction may be carried out at temperatures between 0° C. and 300° C., preferably between 60 to 230° C. and most preferably between 80 and 180° C.

The reaction may be also carried out in the presence of an acidic catalyst. The acidic catalyst may be an inorganic or organic Lewis acid or an inorganic or organic Bronsted acid. Examples for an acidic catalyst may be phosphoric acid, trifluoroacetic acid, oxalic acid, methane sulfonic acid, p-toluene sulfonic acid, trifluoromethane sulfonic acid, benzene sulfonic acid, hydrochloric acid or sulfuric acid. Effectful catalysts are also acid anhydrides like trifluoromethanesulfonic acid anhydride, methanesulfonic acid anhydride, acetic anhydride. Examples for Lewis acids are phosphoryl chloride, CuCl$_2$, ZnCl$_2$, LaCl$_3$, CrCl$_3$, FeCl$_3$, AlCl$_3$, HfCl$_4$, TiCl$_4$, scandium trifluoromethanesulfonate Sc(OTf)$_3$ as well as their hydrates. Acid ion exchangers are also suitable.

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

The UV absorbers according to the present invention are preferably used in the dissolved state (soluble organic filters, solubilized organic filters).

The compounds of the present invention show an excellent solubility behavior in cosmetic oils as listed in the Table 2 below:

TABLE 2

Solubility behaviour [%] of the compounds of the present invention

| Structure | Solvent | | | | | | | |
|---|---|---|---|---|---|---|---|---|
| | (Water) | Cyclomethicone | Finsolve TN | Mygliol | Propyleneglycol | Mineral Oil | Polydecene | Jojoba Oil |
| [Structure 1: bis(2-ethylhexyl)amino-cyclohexenylidene-malononitrile] | 0.000 | 0.540 | >50 | >50 | 0.766 | 1.514 | 0.734 | >50 |
| [Structure 2: bis(2-ethylhexyl)amino-5,5-dimethylcyclohexenylidene-malononitrile] | 0.000 | 0.509 | >5 | >5 | 0.361 | 0.569 | 0.367 | 2.470 |

The cosmetic formulations or pharmaceutical compositions according to the present invention may additionally contain one or more than one further UV filter as listed in Table 3.

TABLE 3

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE 10206562 A1 | Ex 1-3 p 10, Ex 4-7 p 11, Ex 8-15 pp 12-14 |
| DE 10238144 A1 | Ex on p 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p 3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorph olino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |

TABLE 3-continued

Suitable UV filter substances which can be additionally used with the UV absorbers according to the present invention

| | |
|---|---|
| EP 1484051 A2 | Formula III-VII on pp18-19, Ex 7-14 on pp 7-9, Ex 18-23 on pp 11-12, Ex 24-40 on pp 14-17; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, pp 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 3686911 B2 | All benzylidene-gamma-butyrolactone derivatives |
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on pp 6-8; |
| US 2005/0136012A1 | Formula 1 on p 2; |
| US 2005/0136014A1 | Formula a-c on p 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formula 1-2 on p 2; formula 3-4 on p 6; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on pp 18-24 |
| WO 04020398 A1 | Ex 1-3 on pp 14-17 |
| WO 04020398 A1 | Formulas I-VI on pp 21-24, Formula IX on p 25; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the UV absorber of formula (1) according to the present invention and optionally further light-protective agents (as described in Table 2) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The UV absorbers of formula (1) according to the present invention or combinations of UV filters are useful to protect skin, hair and/or natural or artificial hair color.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols Esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, super-fatting agents, surfactants, consistency regulators/thickeners and rheology modifiers, polymers, biogenic active ingredients, deodorising active ingredients, anti-dandruff agents, antioxidants, hydrotropic agents, preservatives and bacteria-inhibiting agents, perfume oils, colourants, polymeric beads or hollow spheres as SPF enhancers.

Cosmetic or Pharmaceutical Preparations

Cosmetic or pharmaceutical formulations are contained in a wide variety of cosmetic preparations. There come into consideration, for example, especially the following preparations:

- skin-care preparations, e.g. skin-washing and cleansing preparations in the form of tablet-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;
- foot-care preparations, e.g. foot baths, foot powders, foot creams or foot balsams, special deodorants and antiperspirants or callus-removing preparations;
- light-protective preparations, such as sun milks, lotions, creams or oils, sunblocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gels, sticks or roll-ons;
- antiperspirants, e.g. antiperspirant sticks, creams or roll-ons;
- preparations for cleansing and caring for blemished skin, e.g. synthetic detergents (solid or liquid), peeling or scrub preparations or peeling masks;
- hair-removal preparations in chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, aftershaves or aftershave lotions;
- fragrance preparations, e.g. fragrances (eau de Cologne, eau de toilette, eau de parfum, parfum de toilette, perfume), perfume oils or perfume creams;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hairfoams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

- in the form of liquid preparations as a W/O, O/W, O/W/O, W/O/W or PIT emulsion and all kinds of microemulsions,
- in the form of a gel,
- in the form of an oil, a cream, milk or lotion,
- in the form of a powder, a lacquer, a tablet or make-up,
- in the form of a stick,
- in the form of a spray (spray with propellent gas or pump-action spray) or an aerosol,
- in the form of a foam, or
- in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

The cosmetic preparation according to the invention is distinguished by excellent protection of human skin against the damaging effect of sunlight.

PREPARATION EXAMPLES

Example 1

Preparation of the Compound of Formula (101)

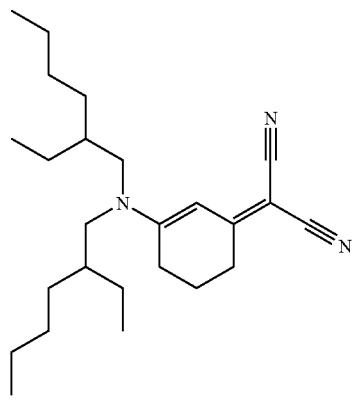

First Step:

9.25 g (0.08 mole) of cyclohexane-1.3-dion were dissolved in 30 mL toluene. The mixture was cooled down to 0° C. and then 19.71 g (0.08 mole) of bis-2-ethylhexylamine were added under stirring. The mixture was heated at 180° C. for 4 hours in an autoclave. After distilling off the solvent and unreacted amine at 150° C. under $1\times10^{-3}$ mbar pressure N,N-bis-2-ethylhexylamino-cyclohexene-3-one is obtained as a darkbrownish oil in yields of 74%.

b.p.=180° C. (0.1 mbar).

Second Step:

3.65 g (0.028 mole) of dimethylsulfate are added dropwise to 8.39 g (0.025 mole) of N,N-bis-2-ethylhexylamino-cyclohexene-3-one. The mixture is stirred for 40 minutes at 100° C. After cooling down to 60° C. a mixture of 1.70 g (0.0252 mole) of malononitrile and 2.76 g (0.0271 mole) of triethylamine in 12 ml of isopropanol are added within 10 minutes. The resulting mixture is then heated at approximately 90° C. for 60 minutes. 2-{3-[Bis-(2-ethyl-hexyl)-amino]-cyclohex-2-enylidene}-malononitrile is then isolated by distillation at 230° C. under 0.1 mbar pressure yielding an orange oil (78%).

Application Examples

Example 2

UV-A/UV-B Every Day Protection Lotion O/W

|  | INCI-Name | % w/w (as supplied) |
|---|---|---|
| Part A | Glyceryl Dilaurate | 2.00 |
|  | Ethylhexyl Palmitate | 6.00 |
|  | Cetyl Alcohol | 1.00 |
|  | Glyceryl Stearate | 2.00 |
|  | Laureth-23 | 1.00 |
|  | Isopropyl Palmitate | 2.00 |
|  | Tribehenin | 0.80 |
|  | Beeswax | 1.50 |
|  | Lanolin Oil | 1.00 |
| Part B | Water | qs to 100 |
|  | Propylene Glycol | 4.00 |
|  | Water (and) Titanium Dioxide (and) Alumina (and) Sodium Metaphosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |
|  | UV-absorber of formula (101) | 8.00 |
| Part E | Water (and) Sodium Hydroxide | qs |

Manufacturing Instruction:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

Example 3

UVA/UVB Sun Protection Lotion, O/W Type

|  | INCI-Name | % w/w (as supplied) |
|---|---|---|
| Part A | Potassium Cetyl Phosphate | 2.00 |
|  | Tricontanyl PVP | 1.00 |
|  | Caprylic/Capric Triglyceride | 5.00 |
|  | C12-15 Alkyl Benzoate | 5.00 |
|  | Cetearyl Isononanoate | 5.00 |
|  | Glyceryl Stearate | 3.00 |
|  | Cetyl Alcohol | 1.00 |
|  | Dimethicone | 0.10 |
|  | Ethylhexyl Methoxycinnamate | 5.00 |
| Part B | Water | qs to 100 |
|  | Glycerin | 3.00 |
| Part C | Steareth-10 Allyl Ether/Acrylates Copolymer | 0.50 |
| Part D | UV-absorber of formula (101) | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for minute. After cooling down to 70° C. part C is added under stirring. After cooling further down to 50° C. part D is incorporated very slowly. At 40° C. part E is added. At room temperature the pH is adjusted with part F to 7.00 and part G is added.

Example 4

UVA/UVB Sun Protection Lotion, O/W Type

|  | INCI-Name | % w/w (as supplied) |
|---|---|---|
| Part A | Potassium Cetyl Phosphate | 2.00 |
|  | Tricontanyl PVP | 1.00 |
|  | Caprylic/Capric Triglyceride | 5.00 |
|  | C12-15 Alkyl Benzoate | 5.00 |
|  | Cetearyl Isononanoate | 5.00 |
|  | Glyceryl Stearate | 3.00 |
|  | Cetyl Alcohol | 1.00 |
|  | Dimethicone | 0.10 |
|  | Ethylhexyl Methoxycinnamate | 5.00 |
| Part B | Water | qs to 100 |
|  | Glycerin | 3.00 |
| Part C | Steareth-10 Allyl Ether/Acrylates Copolymer | 0.50 |
| Part D | UV-absorber of formula (101) | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for minute. After cooling down to 70° C. add part C is added under stirring. After cooling further down to 50° C. part D is incorporated very slowly. At 40° C. part E is added. At room temperature the pH is adjusted with part F to 7.00 and part G is added.

Example 5

W/O Sunscreen Lotion

|  | INCI-Name | % w/w (as supplied) |
|---|---|---|
| Part A | PEG-7 Hydrogenated Castor Oil | 3.00 |
|  | Polyglyceryl-3 Diisostearate | 4.00 |
|  | Microcrystalline Wax | 1.00 |
|  | Magnesium Stearate | 1.50 |
|  | Propylparaben | 0.10 |
|  | Mineral Oil | 15.00 |
|  | Octyldodecanol | 8.00 |
|  | Ethylhexyl Triazone | 1.00 |
|  | Ethylhexyl Methoxycinnamate | 2.00 |
| Part B | Water | qs to 100 |
|  | Water (and) Citric Acid | 0.05 |
|  | Methylparaben | 0.15 |
|  | Magnesium Sulfate | 0.50 |
| Part C | UV-absorber of formula (101) | 9.00 |
|  | Fragrance | qs |

Manufacturing Instruction:

Part A is heated to 80° C. whilst stirring. Part B is added into part A and homogenized with an Ultra Turrax at 11 000 rpm for one minute. After cooling down to 30° C. part C is incorporated.

Example 6

Skin Protection Sunscreen Lotion W/O

|  | INCI-Name | % w/w (as supplied) |
|---|---|---|
| Part A | Polyglyceryl-2 Dipolyhydroxystearate | 3.00 |
|  | Glyceryl Oleate | 3.00 |
|  | Cetearyl Isononanoate | 7.00 |
|  | Hexyl Laurate | 6.00 |
|  | Dicaprylyl Ether | 6.00 |
|  | Propylparaben | 0.10 |
|  | Hexyldecanol | 3.00 |
|  | Magnesium Stearate | 1.00 |
|  | Beeswax | 1.00 |
|  | Ethylhexyl Methoxycinnamate | 4.00 |
| Part B | Water | qs to 100 |
|  | Methylparaben | 0.15 |
|  | Magnesium Sulfate | 1.00 |
| Part C | UV-absorber of formula (101) | 6.00 |

Manufacturing Instruction:

Part A is heated separately to 80° C. under gentle stirring. Part B is added to part A and homogenized for one minute at 11000 rpm. After cooling down to 30° C. part C is added under continuous stirring.

Example 7

O/W Emulsion

|  | INCI-Name | % w/w (as supplied) |
|---|---|---|
| Part A | UV-absorber of formula (101) | 3 g |
|  | sesame oil | 10 g |
|  | glyceryl stearate | 4 g |
|  | stearic acid | 1 g |
|  | cetyl alcohol | 0.5 g |
|  | polysorbate 20 | 0.2 g |
| Part B | propylene glycol | 4 g |
|  | propylparaben | 0.05 g |
|  | methylparaben | 0.15 g |
|  | triethanolamine | 0.1 g |
|  | carbomer 934 | 0.1 g |
|  | water | ad 100 ml |

Preparation of the Emulsion

Phase (A):

Firstly, the UV absorber is dissolved in sesame oil. The other components of (A) are added thereto and combined.

Phase (B):

Propylparaben and methylparaben are dissolved in propylene glycol. 60 ml of water are then added, heating to 70° C. is carried out and then carbomer 934 is emulsified therein.

Emulsion:

(A) is slowly added to (B) with vigorous application of mechanical energy. The volume is adjusted to 100 ml by the addition of water.

Example 8

Daily Care Cream, Type O/W

| | INCI name | % w/w (as used) |
|---|---|---|
| Part A | Glyceryl stearate (and) cetearyl alcohol (and) cetyl palmitate (and) cocoglycerides | 4.0 |
| | Ceteareth-12 | 4.0 |
| | Cetearyl alcohol | 2.0 |
| | Dicaprylyl ether | 4.5 |
| | Ethylhexyl stearate | 4.0 |
| | Hexyl laurate | 3.5 |
| | Ethylhexyl triazone | 1.0 |
| | Benzylidene malonate polysiloxane | 2.0 |
| | HDI/trimethylol hexyl-lactone crosspolymer (and) silica | 5.0 |
| | Stearyl dimethicone | 1.0 |
| | Dimethicone | 2.0 |
| | Cetyl alcohol | 0.8 |
| | UV-absorber of formula (101) | 2.0 |
| Part B | Water | q.s. to 100 |
| | Water (and) scleroglucan (and) phenoxyethanol | 2.0 |
| | Glycerol | 2.0 |
| Part C | Steareth-10 allyl ether/acrylate copolymer | 0.45 |
| | Phenoxyethanol (and) methylparaben (and) ethylparaben (and) butylparaben (and) propylparaben (and) isobutylparaben | 0.7 |
| Part D | Aqua (and) tocopheryl acetate (and) caprylic/capric triglyceride (and) polysorbate 80 (and) lecithin | 4.0 |
| Part E | Water (and) sodium hydroxide | q.s. |
| | Fragrance | q.s. |

Preparation Procedure:

Part A and part B are heated separately to 80° C. Part A is poured into part B, whilst stirring continuously. Afterwards the mixture is homogenized with an Ultra Turrax at 11 000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

Example 9

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | UV-absorber of formula (101) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. The mixture is cooled to 60° C. and part C and part D are incorporated. The mixture is homogenised again for a short time (5 sec./11 000 rpm) and further cooled, with moderate stirring. At room temperature, the pH is adjusted with sodium hydroxide solution to between 5.5 and 6.0. Finally, fragrance is added.

Example 10

Daily Care UV-Protection Lotion

| | INCI name | % w/w (as used) |
|---|---|---|
| Part A | Oleth-3 phosphate | 0.6 |
| | Steareth-21 | 2.5 |
| | Steareth-2 | 1.0 |
| | Cetyl alcohol | 0.8 |
| | Stearyl alcohol | 1.5 |
| | Tribehenin | 0.8 |
| | Isohexadecane | 8.0 |
| | UV-absorber of formula (101) | 5.0 |
| Part B | Water | q.s. to 100 |
| | Glycerol | 2.0 |
| | Methylene bis-benzotriazolyl tetramethylbutylphenol (and) aqua (and) decyl glucoside (and) propylene glycol (and) xanthan gum | 3.0 |
| | Disodium EDTA | 0.1 |
| Part C | Water | 20.0 |
| | Diazolidinyl urea (and) iodopropynyl butylcarbamate | 0.15 |
| | Propylene glycol | 4.0 |
| Part D | Sodium acrylate copolymer (and) liquid paraffin (and) PPG-1 trideceth-6 | 1.5 |
| | Cyclopentasiloxane | 4.5 |
| | PEG-12 dimethicone | 2.0 |
| | Tocopheryl acetate | 0.45 |
| | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11 000 rpm for 30 sec. Allow to cool to 65° C. and incorporate SALCARE® SC91. At a temperature below 50° C., add part C. At 35° C. or below, incorporate vitamin E acetate and subsequently adjust the pH with citric acid. At room temperature, add part E.

Example 11

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | UV-absorber of formula (101) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. The mixture is cooled to 60° C., and part C and part D are incorporated. The mixture is homogenised again for a short time (5 sec./11 000 rpm). After further cooling, with moderate stirring, the pH is adjusted with sodium hydroxide at room temperature. A solution between pH 5.50 and 6.00 is obtained. Finally, fragrance is added.

Example 12

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of UV-absorber of formula (101) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. After cooling 60° C., part C and part D are incorporated. The mixture is homogenised again for a short time (5 sec./11 000 rpm). After further cooling, with moderate stirring, the pH is adjusted at room temperature with sodium hydroxide solution to between 5.50 and 6.00. Finally, fragrance is added.

Example 13

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of UV-absorber of formula (101) (50%) and benzylidene camphor, CAS Reg. No. 36861-47-9 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. After cooling to 60° C., part C and part D are incorporated. The mixture is homogenised again for a short time (5 sec./11 000 rpm). After further cooling, with moderate stirring, the pH is adjusted at room temperature with sodium hydroxide. A solution between pH 5.50 and 6.00 is obtained. Finally, fragrance is added.

The invention claimed is:
1. A compound of formula

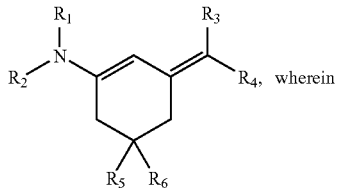

(1)

wherein $R^1$ and $R^2$ independently from each other are branched $C_4$-$C_{22}$alkyl; or branched $C_4$-$C_{12}$alkenyl;
$R^3$ and $R^4$ are cyano; and
$R^5$ and $R^6$ independently from each other are hydrogen; $C_1$-$C_6$alkyl; or
$C_5$-$C_8$cycloalkyl which may be substituted by one or more than one $C_1$-$C_4$alkyl.

2. A compound according to claim 1, wherein in formula (1)
$R^1$ and $R^2$ are identical; and
$R^3$, $R^4$, $R^5$, and $R^6$ are as defined in claim 1.

3. A compound according to claim 1, wherein in formula (1)
$R^1$ and $R^2$ are selected from the group consisting of 1-methylpropyl; 1,3-dimethylbutyl; 2-methylbutyl; 1,1,3,3-tetramethylbutyl; 3-methylbutyl; 7-methyloctyl; 2-ethylhexyl; 4-methylcyclohexyl; and 2-methyl-2-propene.

4. A method for the protection of human hair and skin against the damaging effect of UV radiation wherein said method comprises applying to said hair and skin an effective amount of a compound of formula (1) according to claim 1.

5. A cosmetic preparation comprising at least one compound of formula (1) according to claim 1 together with cosmetically tolerable carriers or adjuvants.

* * * * *